United States Patent [19]

Inamoto et al.

[11] 3,966,800

[45] June 29, 1976

[54] 1-CARBOXYMETHYL-3-CHLOROADAMANTANE

[75] Inventors: Yoshiaki Inamoto, Wakayama; Takeji Kadono, Kainan; Naotake Takaishi, Wakayama, all of Japan

[73] Assignee: Kao Soap Co., Ltd., Tokyo, Japan

[22] Filed: Nov. 29, 1974

[21] Appl. No.: 528,399

Related U.S. Application Data

[63] Continuation-in-part of Ser. No. 410,508, Oct. 29, 1973, Pat. No. 3,897,479.

[30] Foreign Application Priority Data

Oct. 30, 1972 Japan............................. 47-108602

[52] U.S. Cl. .......................................... 260/514 G
[51] Int. Cl.$^2$........................................ C07C 61/38
[58] Field of Search...................... 260/468 G, 514 G

[56] References Cited
UNITED STATES PATENTS 3,767,694   10/1973   Narayanan et al................. 260/468

OTHER PUBLICATIONS

Bott, Chem. Ber. 101 564 (1968).

*Primary Examiner*—Robert Gerstl
*Attorney, Agent, or Firm*—Woodhams, Blanchard and Flynn

[57] ABSTRACT

The compound, 1-carboxymethyl-3-chloroadamantane, is useful as a plant growth stimulator and as an intermediate for preparing other useful compounds. The compound, 1-carboxymethyl-3-chloroadamantane, is prepared by reacting 1-aoamantylacetic acid with a hydrogen halide or a metal halide, in 70-98 wt. % sulfuric acid, in carbon tetrachloride or cyclohexane, and in the presence of t-butanol.

1 Claim, No Drawings

1-CARBOXYMETHYL-3-CHLOROADAMANTANE

CROSS-REFERENCE TO RELATED APPLICATION

This application is a continuation-in-part of pending application Ser. No. 410 508, filed Oct. 29, 1973, now U.S. Pat. No. 3,897,479.

BACKGROUND OF THE INVENTION

1. FIELD OF THE INVENTION

This invention relates to the compound 1-carboxymethyl-3-chloroadamantane.

2. DESCRIPTION OF THE PRIOR ART

Although a number of halogenated derivatives of adamantane are known, insofar as we are aware, the compound 1-carboxymethyl-3-chloroadamantane was not known prior to our invention.

SUMMARY OF THE INVENTION

We have discovered the compound 1-carboxymethyl-3-chloroadamantane. It can be prepared by a commercially advantageous process, in a high purity, at a high yield, by the reaction of 1-adamantyl-acetic acid with hydrogen halide or metal halide in concentrated sulfuric acid and carbon tetrachloride or cyclohexane solvent, in the presence of t-butanol.

A preferred process for preparing the compound according to the present invention is based on the following chemical reactions:

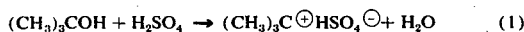

$$(CH_3)_3COH + H_2SO_4 \rightarrow (CH_3)_3C^{\oplus}HSO_4^{\ominus} + H_2O \quad (1)$$

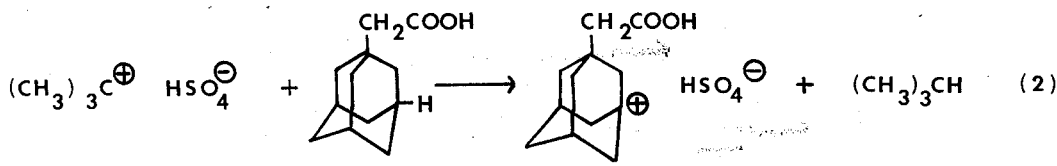

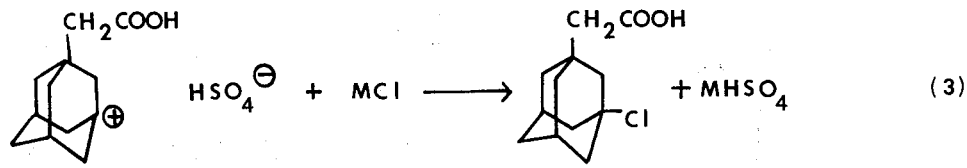

wherein M is hydrogen, an alkali metal, an alkaline earth metal, boron or aluminum.

In carrying out the process, (1) a hydrogen halide gas is introduced into, or a metal halide is added to, a mixture of (2) concentrated sulfuric acid, (3) carbon tetrachloride or cyclohexane and (4) 1-adamantyl-acetic acid of the formula

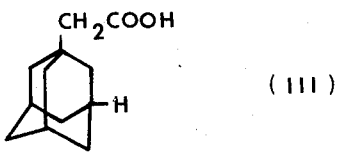

(III)

while (5) t-butanol is added thereto incrementally, e.g., dropwise, with mixing such as stirring at a definite reaction temperature. Such a mode and sequence of adding the reagents is essential. If t-butanol is added not dropwise, but rather is added in one quantity, of if the order of the addition of the reagents is changed or reversed, the yield of the final product is reduced extremely.

As chlorine sources represented by MX in above reaction formula (3), various metal chlorides soluble in sulfuric acid such as alkali metal chlorides, alkaline earth metal chlorides, boron chloride and aluminum chloride can be used in addition to hydrogen chloride.

The concentration of the sulfuric acid used in the process is 70 to 98 wt. %. If sulfuric acid of a concentration less than 70% is used, the yield is substantially 0 (zero). If sulfuric acid of a concentration higher than 98% is used, a side oxidation reaction also occurs to produce adamantanone-2. The preferred concentration range of the sulfuric acid is 90–98%. The sulfuric acid is used in a quantity of 10 to 80 parts by weight, preferably 20 to 60 parts by weight, per one part of t-butanol. The use of sulfuric acid in a quantity less than 10 parts per one part of t-butanol is not preferred, because water formed by the reaction with t-butanol dilutes the sulfuric acid to decrease the concentration thereof to a value lower than the effective lower limit thereof.

The quantity of carbon tetrachloride or cyclohexane used in the process is 10 to 30 parts by weight per one part of the starting adamantane (III). One of the roles of carbon tetrachloride or cyclohexane in the process is to dissolve the solid adamantane and to disperse the adamantane in concentrated sulfuric acid. The use of carbon tetrachloride or cyclohexane is indispensable with respect to the improvement in yield of the compound of the invention, according to this process.

The quantity of t-butanol used is 1 to 5 moles, preferably 2 to 3 moles, per one mole of the starting adamantane (III). The t-butanol preferably is mixed with a further quantity of the solvent, i.e. carbon tetrachloride or cyclohexane, because t-butanol has a high melting point and may be solid at room temperature, and it is required to be dissolved in a solvent for its dropwise addition.

The amount of the hydrogen chloride or metal salt thereof used is in the range of 5 to 20 moles per one mole of the starting adamantane (III). It is desirable that at least one equivalent (mole), preferably 2 to 3 equivalents, of the hydrogen chloride or metal salt thereof, per one mole of the starting adamantane (III), shall have been added to the reaction system before the completion of the addition of t-butanol. If the quantity of hydrogen chloride or metal salt thereof is less than 1 equivalent, the yield of the final product is poor and the byproduction of isobutyladamantane becomes appreciable.

The reaction temperature is 0° to 20°C, preferably 5° to 10°C.

During the reaction period, the total time required for adding the mixture to t-butanol and carbon tetrachloride or cyclohexane is from about 10 to 60 minutes, preferably at least 15 minutes. The rate of the introduction of the hydrogen chloride or salt should be higher than 6 moles/hr., preferably 12 moles/hr. per mole of starting adamantane (III). After the addition of t-butanol is completed the remaining predetermined amount of the hydrogen chloride or salt should be added and also the reaction should be preferably continued for at least one hour after completion of the addition of t-butanol.

The most simple method of isolation of 1-carboxymethyl-3-chloroadamantane from the reaction mixture is as follows:

The reaction mixture is poured onto broken ice pieces. The extraction is effected with an inert solvent. The extract is washed successively with aqueous sodium bicarbonate and water. After drying with calcium chloride, the solvent is concentrated to obtain the crude chloride. Although the chloride thus obtained is sufficiently pure, the most advantageous method of further purification is distillation or recrystallization.

The compound 1-carboxymethyl-3-chloroadamantane can be used for stimulating the growth of a wide variety of chlorphyllproducing plants, including monocotyledonous and dicotyledonous species grown for agricultural use or as ornamentals belonging to such plant families as Rosaceae, Solanaceae, Gramineae, Cucurbitaceae, Leguminosae, Malvaceae and Compositae.

The activity of 1-carboxymethyl-3-chloroadamantane as a plant growth stimulant is evidenced by such effects as increased height of the plants, increased number of leaves, increased length of internodes, increased weight, and increased ability to utilize nutrients in nutrient deficient or depleted soil as expressed by a dark green color of the leaves compared with chlorotic leaves of the untreated plants.

The compound may be applied to seeds by tumbling the chemical with the seed, either alone or in admixture with a powdered solid carrier, to coat the seeds. Typical powdered solid carriers are the various mineral silicates, e.g. mica, talc, pyrophillite, and clays. The compound may also be applied to the seeds in admixture with a conventional surface-active wetting agent, with or without additional powdered solid carrier, as by first wetting the mixture with a small amount of water and then tumbling the seeds in the slurry. The surface-active wetting agents that may be used with the compound may be any of the conventional anionic, non-ionic, or cationic surface-active agents. Such surface-active agents are well known. As a seed treatment, the amount of the compound coated on the seeds will be 2 to 8 ounces per hundred pounds of the seed. As a soil treatment the compound may be applied as a dust in admixture with sand or dirt or a powdered solid carrier such as a mineral silicate, with or without an additional surface-active wetting agent, to the furrows with the planting of the seeds, or the compound may be applied as an aqueous spray, if desired including a surface-active dispersing agent, or a surface-active dispersing agent and a powdered solid carrier, to the seed rows before, or with, or after planting the seeds. As a soil treatment, the amount of the compound applied to the seed rows will be from 0.5 to 5 pounds per acre applied to the seed rows the equivalent of an area 2 inches wide and 2 inches deep to parallel rows in one direction a distance of 40 inches apart. Also, as a soil treatment, the compound may be applied broadcast as a similar dust or aqueous spray with an application rate of 1 to 10 pounds per acre. As a foiliage treatment, the compound may be applied to growing plants at a rate of 0.5 to 5.0 pounds per acre. Such application is generally as an aqueous spray which also contains a surface-active dispersing agent, or a surface-active dispersing agent and a powdered solid carrier.

The use of the process of this invention may lead to better harvest results and to acceleration in the ripening of such crop plants as cucumbers, corn and beans by stimulated growth. Their use is of particular importance for promoting the growth of young plants. It permits, for example, the growth of succulent fruits of vines, such as cucumbers and beans, to be stimulated so that these vegetables can be marketed at an earlier date and greenhouses can be used more intensively than is ordinarily possible.

The present invention will be further described by reference to the following illustrative Examples. In the Examples, the melting points are uncorrected.

EXAMPLE 1

18 Grams of sodium chloride were added in about 20 equal portions to a mixture of 3 g of 1-adamantyl-acetic acid, 60 ml. of carbon tetrachloride and 200 g of 96% sulfuric acid which was kept at 5°–10°C by external cooling under thorough stirring over a period of 6 hours while a mixture of 9 g of t-butanol and 20 ml. of carbon tetrachloride was added thereto dropwise over 30 minutes. The reaction mixture was poured onto 300 g of broken ice pieces. The crystalline precipitate was filtered out, washed with water sufficiently and air-dried to obtain 3.2 g (yield: 91.1%) of crude 1-carboxymethyl-3-chloroadamantane.

The product was recrystallized from a mixture of water and methanol (3:7) to obtain the pure product of m.p. 182°–183.5°C. Elementary analysis:
Calcd. for $C_{12}H_{17}O_2Cl$: C 63.02; H 7.49; Cl 15.50%
Found: C 62.8; H 7.3; Cl 15.8%
IR Spectrum ($cm^{-1}$, KBr tablet):
  3200–2400; $\nu$ O—H
  2950 (shoulder), 2900, 2850; $\nu$CH
  1700; $\nu$C=O
  1450, 1430, 1410; $\delta$CH
NMR Spectrum ($\delta$, $CD_3SOCD_3$)
  1.55 (doublet, 6H); hydrogen in $\delta$-position from Cl group
  2.03 (doublet, 8H)
  2.05–2.25 (2H); hydrogen in bridgehead position
Mass spectrum (m/e (relative intensity))
  230 (6); P+2
  228 (15); P
  210 (6); P—$H_2O$
  193 (100); P—(Cl)
  169 (74); P—($CH_2COOH$)
  133 (48)

EXAMPLE 2

1-Carboxymethyl-3-chloroadamantane, according to the present invention, exhibits plant growth promoting properties, as shown by the following test.

Cucumber seeds were placed onto a sheet of filter paper moistened with water, in a petri dish. After 35 hours incubation at 25°C in the dark, the cucumber roots had a length of about 1 mm on an average. Sets of 10 seeds thus germinated were placed in a 1 liter beaker on a double sheet filter paper bed moistened with a test solution containing a specified concentration of 1-carboxymethyl-3-chloroadamantane and 0.05% Tween 80/Span 80 mixture (70/30). After the beakers were kept at 25°C in the dark for 7 days, the lengths of the stems and roots were measured. The results are summarized in Table 1.

Table 1

| Concentration of 3-chloroadamant-1-ylacetic acid (ppm) | Length of stems and roots of cucumber in the presence of 1-carboxymethyl-3-chloroadamantane | | | |
|---|---|---|---|---|
|  | 500 | 50 | 5 | 0.5 |
| Length of Stem* | 125# | 112 | 103 | 105 |
| Length of Root* | 122# | 110 | 100 | 98 |

*Relative to a control experiment using a solution containing only 0.05% Tween 80/Span 80, in which the length of stems and roots were taken as 100, respectively.

Differences among the values are significant at 5% level.

In addition to the above-mentioned utility as a plant growth stimulator, the compound (IV) of this present invention is useful as an intermediate for preparing other useful compounds.

Adamantane diacetic acids (V) is derived from 1-carboxymethyl-3-chloroadamantane (IV) by the reaction thereof with 1,1-dichloroethylene, which reaction is known as Bott reaction described in Chem, Ber, vol, 101, page 564–573 (1968). The adamantane diacetic acids (V) thus obtained is further useful for preparing a polyamide (VI) by the reaction thereof with an organic diamine in the presence of thionyl chloride, which reaction was described in U.S. Pat. No. 3 464 957. Furthermore, the diamine (VII) of the adamantane compound (IV) is derived from the diacetic acid (V), which was described in U.S. Pat. No. 3 748 359.

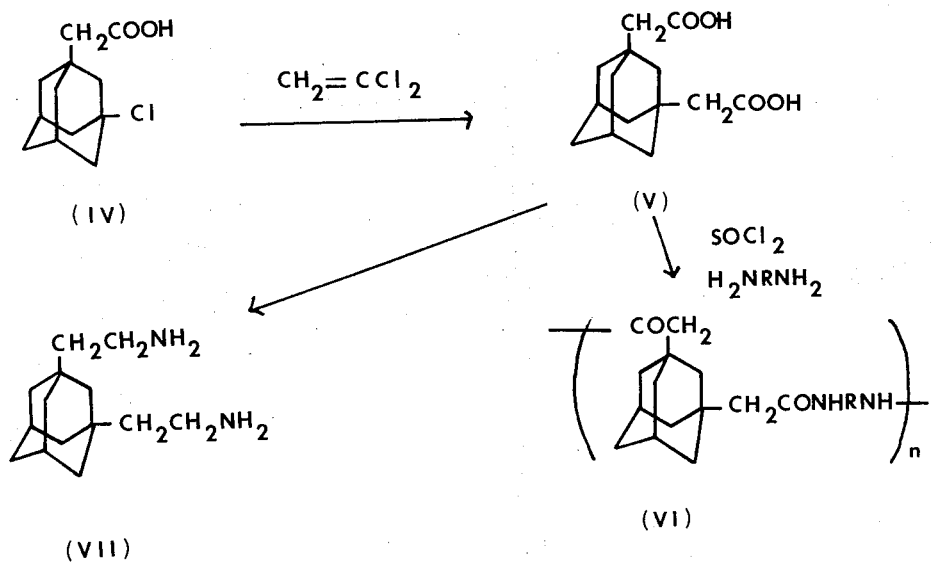

The embodiments of the invention in which an exclusive property of privilege is claimed are defined as follows:

1. 1-Carboxymethyl-3-chloroadamantane.

* * * * *